US00PP35491P2

(12) United States Plant Patent
Berry

(10) Patent No.: US PP35,491 P2
(45) Date of Patent: Nov. 21, 2023

(54) ***HIBISCUS* PLANT NAMED 'JBG 19034'**

(50) Latin Name: *Hibiscus rosa-sinensis*
Varietal Denomination: JBG 19034

(71) Applicant: Capstone Plants, Inc., Grand Saline, TX (US)

(72) Inventor: James Berry, Emory, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 18/203,219

(22) Filed: May 30, 2023

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
See application file for complete search history.

*Primary Examiner* — Susan McCormick Ewoldt
(74) *Attorney, Agent, or Firm* — The Webb Law Firm

(57) ABSTRACT

A new and distinct *Hibiscus* plant having intense orange colored flowers with a prominent eye and a compact growth habit.

2 Drawing Sheets

Botanical classification: *Hibiscus rosa-sinensis.*
Varietal denomination: 'JBG 19034'.

BACKGROUND OF THE INVENTION

The present invention comprises a new and distinct *Hibiscus* plant having the varietal name 'JBG 19034'. The new variety is the result of a planned breeding program with the purposes of developing *Hibiscus rosa-sinensis* plants that exhibit whitefly and bacterial and fungal leaf spot resistance, propagation and production efficiencies, durable and exotic flowers, and abundant flowering. 'JBG 19034' is the result of a cross conducted in Grand Saline, Texas between *Hibiscus rosa-sinensis* varieties 'AH-64' (female parent, unpatented) and 'JBG MH-17' (male parent, U.S. Plant Pat. No. PP34,664). The new variety was selected in April of 2018 in Grand Saline, Texas and the first asexual reproduction of the new variety was conducted by semi-hardwood cuttings in September of 2018 in Grand Saline, Texas. 'JBG 19034' has been trial and field tested and has been found to retain its distinctive characteristics and remain true to type through successive propagations. The present invention has not been evaluated under all possible environmental conditions. However, it has been found to thrive in production and adapt well to the environment in Homestead, Florida. The phenotype may vary with variations in environment without a change in the genotype of the plant.

'JBG 19034' is similar to its female parent in petal shape and ruffling, having a dark flower eye, and in growth rate. 'JBG 19034' differs from its female parent in flower color (the female parent has pink flowers) and exhibiting smaller foliage. 'JBG 19034' is similar to its male parent in flower color and shape, having a large, dark flower eye, and exhibiting rich green colored foliage. However, 'JBG 19034' differs from its male parent in having smaller flowers and petals, as well as a smaller overall plant size and slower growth rate.

When 'JBG 19034' is compared to *Hibiscus rosa-sinensis* variety named 'MH-05' (unpatented), both varieties have an orange flower color, similar male parentage, and low to moderate growth rate. However, 'JBG 19034' has a darker colored and more prominent flower eye, the petals of 'MH-05' are more ruffled, and the flowers of the new variety are longer lasting than those of 'MH-05'.

The following traits distinguish 'JBG 19034' as a new and distinct cultivar from other *Hibiscus* varieties known to the breeder:

1. Intense orange flower color:
2. Naturally compact growth habit;
3. High quantity of open flowers at the same time;
4. Shiny and waxy foliage; and
5. Multiple buds present on a single axle.

DESCRIPTION OF THE DRAWINGS

The accompanying photographic images illustrate the new variety at approximately four months of age, with the colors being as nearly true as is possible with color illustrations of this type.

DESCRIPTION OF THE PLANT

Figure 1:
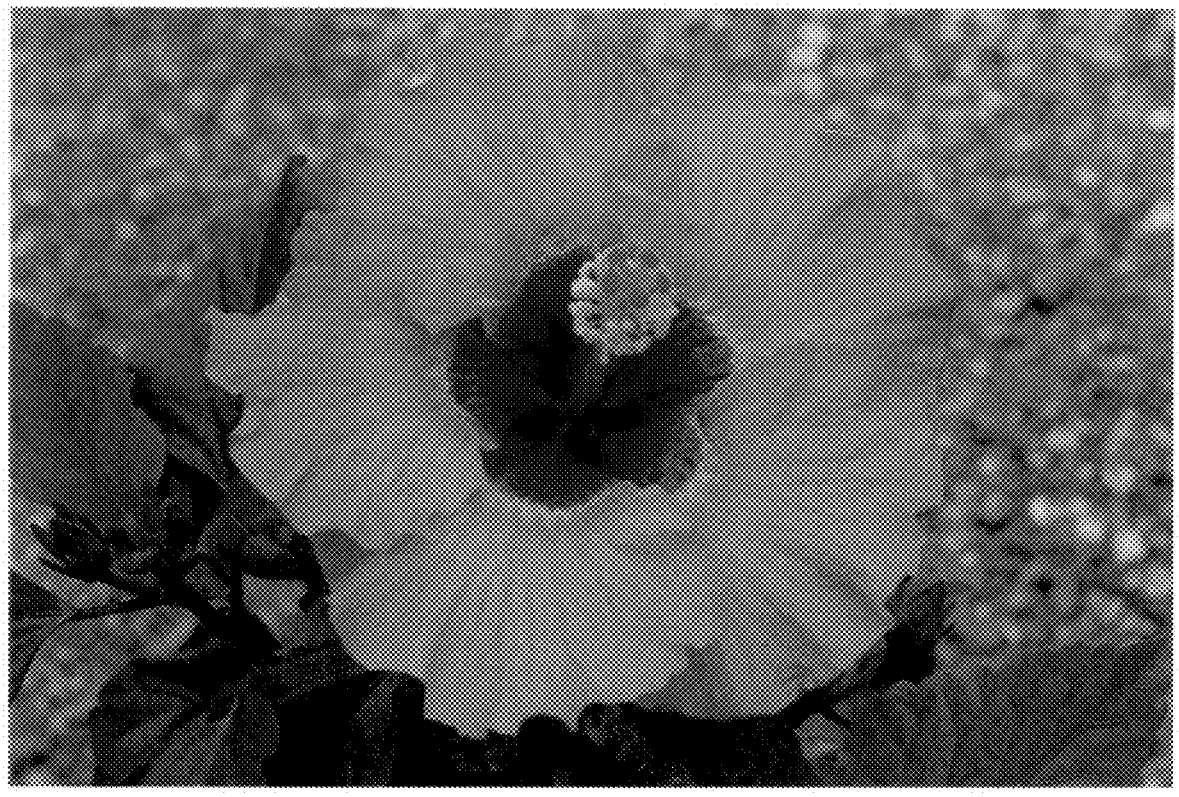
FIG. 1 illustrates a close-up view of a flower of the new variety.
Figure 2:
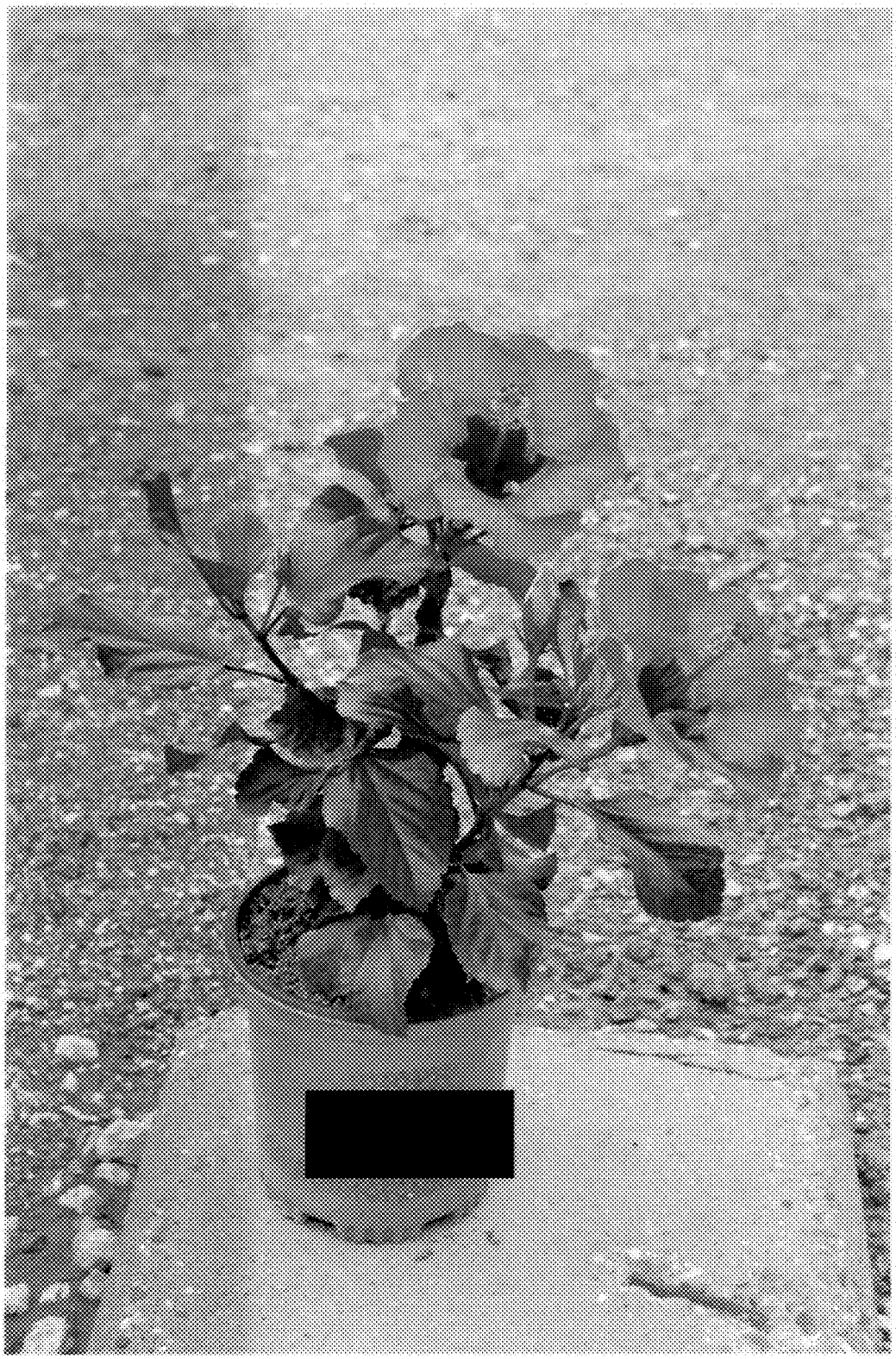
FIG. 2 illustrates an entire plant of the new variety.

The following detailed description sets forth the characteristics of the new variety. The plants were grown in 15 cm containers in a heated greenhouse with a minimum temperature of approximately 13° C. and about 30% light shade in the summer months. The color readings and measurements were taken indoors under fluorescent lights with natural light from a window nearby on approximately four month old plants. Color references are primarily to The 1995 R.H.S. Colour Chart of The Royal Horticultural Society of London, 3rd Edition, except where general color terms are used.

PLANT

Time to initiate roots: About 12 days at an average of 24° C.

Time to develop roots: About 50 days at an average of 21-24° C.

Time to produce a finished flowering plant from a rooted cutting: About 12-16 weeks in a 1 gallon/20.0 cm diameter container.

Specific disease/pest resistance: Resistance to whitefly (*Trialeurodes vaporariorum*) and bacterial leaf spot (*Pseudomonas* spp.).

Heat/cold tolerance: Thrives above 13° C., but expires at temperatures of 0° C. and below.

Drought tolerance: Moderate to none.

Plant:

*Type.*—Tropical, ornamental shrub.

*Habit.*—Compact with good branching.

*Height.*—22.9 cm from the top of the pot to the top of the plant.

*Spread.*—35.6 cm.

*Vigor.*—Low to moderate.

*Rooting.*—Coarse and well-branched.

Stem:

*Number per plant.*—2.

*Length.*—19.1 cm.

*Width.*—1.0 cm.

*Texture.*—Immature: Slightly textured. Mature: Heavily textured and rough.

*Strength.*—Firm.

*Branch number.*—7.

*Internode length.*—2.5 cm.

*Color.*—Immature: 183A and 144B. Mature: 199B.

*Stipules.*—Number per node: 2. Shape: Spinose. Length: 8.0 mm. Width: 1.0 mm. Surface texture: Smooth. Apex: Acute. Base: Linear. Margin: Entire. Color: 143A at the tip and 59A at the base.

Foliage:

*Arrangement.*—Alternate.

*Size of leaf.*—Length: 9.5 cm. Width: 7.6 cm.

*Shape of leaf* (*generally*).—Ovate.

*Shape of apex.*—Acute.

*Shape of base.*—Rounded.

*Texture.*—Upper surface: Smooth and waxy, with a slight texture from venation. Lower surface: Slightly rough, with pubescence and texture from venation.

*Margin type.*—Crenate.

*Color.*—Young leaves: Upper surface: 141A. Lower surface: 146A. Mature leaves: Upper surface: 135A. Lower surface: 146A.

*Veins.*—Venation type: Palmate. Color: Upper surface: 137A. Lower surface: 137C.

*Petole.*—Length: 3.2 cm. Diameter: 3.0 mm. Texture: Slightly textured. Color: 143A in the lower surface center and 187A on the upper surface and remainder of the lower surface.

FLOWERS

Buds (described at approximately 4 days from opening):

*Shape.*—Elliptical.

*Diameter.*—2.1 cm.

*Length.*—4.9 cm.

Natural flowering season: Year round in Grand Saline, Texas.

Flower type and habit: Single with slightly overlapping petals.

Fragrance: None.

Flowers:

*Number per stem.*—1-4.

*Overall depth.*—3.0 cm.

*Overall diameter.*—13.5 cm.

*Shape.*—Rotate.

*Lastingness.*—2 days on the plant.

*Petals.*—Number: 5. Arrangement: Simple. Length: 8.3 cm. Width: 7.6 cm. Shape: Ovate. Apex: Obtuse. Base: Acute. Margin: Entire. Texture/appearance: Upper surface: Smooth and velvety. Lower surface: Light and soft, with venation texture present. Color: When opening: Upper surface: 30B on edge; 59A eye color. Lower surface: 34C on one side; 164C on overlapping edge. Fully opened: Upper surface: 30C at tip; 187B eye color; 44C edging around eye with 20B in between the two. Lower surface: 30D at tip; 184D eye color; 164C edging petals overlap slightly.

*Calyx.*—Form: Fused. Overall length: 2.9 cm. Overall diameter: 2.1 cm. Sepals/calyx lobes: Number: 5. Shape: Lanceolate. Apex: Acute. Margin: Entire. Texture: Smooth with slightly textured edges. Color: Outer surface: 143A. Inner surface: 146D.

*Epicalyx.*—Length: 1.9 cm. Width: 4.0 mm. Texture: Smooth with slightly textured edges. Color: 143A. Sepal-like bracts: Not present.

*Bracts.*—Not present.

*Peduncle.*—Length: 10.0 mm. Diameter: 5.0 mm. Strength: Very firm. Angle: Approximately 20°. Texture: Slightly coarse. Color: 143B.

Reproductive organs:

*Gynoecium.*—Pistils: Number: 1. Length: 8.3 cm. Stigma: Number: 5. Shape: Round. Length: 4.0 mm. Diameter: 4.0 mm. Color: 44A. Style: Length: 6.5 cm. Width: 4.0 mm. Color: The majority is 53A; 52C towards top of the style; 8C striations present. Ovary: Shape: Cylindrical, with a rounded top. Length: 9.0 mm. Width: 6.0 mm. Color: 4C.

*Androecium.*—Stamens: Number: 87. Position: Below the stigma on the style. Anther: Shape: U-shaped. Diameter: 1.0 mm. Color: 17C. Filament: Length: 8.0 mm. Width: 1.0 mm. Color: 58B. Pollen: Color: 17C. Amount (generally): Moderate to high.

SEEDS

Seeds: None produced.

I claim:

1. A new and distinct variety of *Hibiscus* plant named 'JBG 19034', substantially as illustrated and described herein.

* * * * *